United States Patent
Sablone et al.

(10) Patent No.: US 10,967,623 B2
(45) Date of Patent: Apr. 6, 2021

(54) APPARATUS AND METHOD FOR PRODUCING ELASTICIZED COMPOSITE SIDE PANELS AND NON-ELASTICIZED SIDE PANELS FOR ABSORBENT SANITARY ARTICLES

(71) Applicant: Fameccanica.Data S.p.A., San Giovanni Tetino (IT)

(72) Inventors: Gabriele Sablone, Pescara (IT); Alessandro D'Andrea, Pescara (IT)

(73) Assignee: FAMECCANICA.DATA S.P.A., San Giovanni Teatino (IT)

( * ) Notice: Subject to any disclaimer, the term of this patent is extended or adjusted under 35 U.S.C. 154(b) by 0 days.

(21) Appl. No.: 16/023,215

(22) Filed: Jun. 29, 2018

(65) Prior Publication Data

US 2019/0381778 A1    Dec. 19, 2019

(30) Foreign Application Priority Data

Jun. 30, 2017    (IT) .................. 102017000073474

(51) Int. Cl.
*B32B 37/22*    (2006.01)
*B32B 7/022*    (2019.01)
(Continued)

(52) U.S. Cl.
CPC ............... *B32B 37/22* (2013.01); *B32B 3/14* (2013.01); *B32B 7/022* (2019.01);
(Continued)

(58) Field of Classification Search
CPC   B32B 37/22; B32B 7/022; B32B 3/14; B32B 38/0004; B32B 38/0012;
(Continued)

(56) References Cited

U.S. PATENT DOCUMENTS 5,683,533 A * 11/1997 Keighley .......... A61F 13/15699
156/204
5,705,013 A * 1/1998 Nease ............... A61F 13/15699
156/163
(Continued)

FOREIGN PATENT DOCUMENTS

EP    2561845 A1    2/2013

OTHER PUBLICATIONS

Italian Search Report and Written Opinion dated Mar. 22, 2018 for Application No. IT201700073474.

*Primary Examiner* — Christopher T Schatz
*Assistant Examiner* — Cynthia L Schaller
(74) *Attorney, Agent, or Firm* — Patterson + Sheridan, LLP (57) ABSTRACT

A method for producing elasticized composite side panels and non-elasticized side panels, comprising: feeding a continuous web of a first non-extensible material having longitudinal side edges along a first direction parallel to a longitudinal axis of said web, forming in said web, in a position within said longitudinal edges, and at a pitch, a plurality of oblong openings having a major axis substantially parallel to the longitudinal axis of said web, each opening having a maximum transverse dimension with a first length, a maximum longitudinal dimension with a second length, and two longitudinal end zones, forming a plurality of rectangular elements of elastic material having in a relaxed condition two minor sides with a first dimension greater than said first length and two major sides with a second dimension at least equal to said second length of said oblong openings, said elements of elastic material being elastically extensible at least along the first dimension, transferring each of said rectangular elements of elastic material in a relaxed condition onto said continuous web at each oblong opening and in a substantially centered position (Continued)

with respect thereto, welding each rectangular element to said continuous web along at least the respective longitudinal edges superimposed on the longitudinal edges of each oblong opening, so as to form a continuous composite web, making transverse cuts at predetermined intervals on said continuous composite web so as to remove transverse portions from said continuous composite web comprising the longitudinal end zones of each oblong opening and the corresponding minor sides of each respective rectangular element of elastic material, to form alternately individual elasticized composite panels comprising said elastic material and individual non-elasticized panels not comprising said elastic material.

8 Claims, 5 Drawing Sheets (51) Int. Cl.
*B32B 3/14* (2006.01)
*B32B 38/00* (2006.01)
*B32B 38/04* (2006.01)

(52) U.S. Cl.
CPC ...... *B32B 38/0004* (2013.01); *B32B 38/0012* (2013.01); *B32B 38/04* (2013.01); *B32B 2038/047* (2013.01); *B32B 2250/02* (2013.01); *B32B 2307/51* (2013.01); *B32B 2307/726* (2013.01); *B32B 2555/02* (2013.01)

(58) Field of Classification Search
CPC .............. B32B 38/04; B32B 2038/047; B32B 2250/02; B32B 2307/51; B32B 2307/726; B32B 2555/02; A61F 13/15585; A61F 13/15756; A61F 13/5633
See application file for complete search history.

(56) References Cited

U.S. PATENT DOCUMENTS

| | | |
|---|---|---|
| 9,398,986 B2 | 7/2016 | Pasqualoni et al. |
| 2010/0221496 A1* | 9/2010 | de Jong .............. A61F 13/4902 428/172 |
| 2013/0082418 A1* | 4/2013 | Curro ..................... B29C 55/18 264/288.4 |

* cited by examiner

APPARATUS AND METHOD FOR PRODUCING ELASTICIZED COMPOSITE SIDE PANELS AND NON-ELASTICIZED SIDE PANELS FOR ABSORBENT SANITARY ARTICLES

FIELD OF THE INVENTION

The present invention relates to an apparatus and a method for producing side panels for absorbent sanitary articles.

The present invention has been developed in particular for producing elasticized panels intended to be applied to the waist region of disposable absorbent sanitary articles, for example, of the type for babies or for incontinent adults.

DESCRIPTION OF THE PRIOR ART

Figure 1:
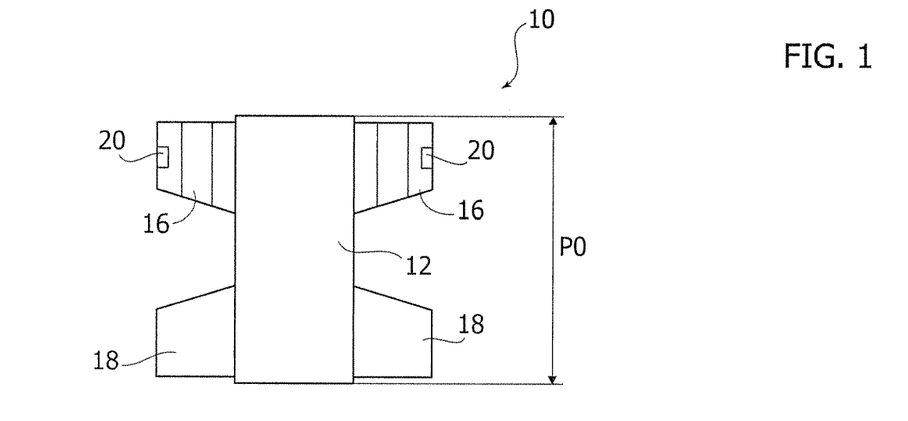
FIG. 1 is a general plan view of a sanitary article wearable as pants provided with side panels of the type described here, shown in an extended position.

In the field of sanitary articles wearable as pants, typically diapers for babies or incontinence pads for adults, the general structure represented, by way of example, in FIG. 1 has been increasingly affirmed, where an article of the type considered here is represented in the unfolded condition and with the surface that is in contact with the user's body facing the observer. The sanitary article 10 illustrated in FIG. 1 comprises front and rear side panels, and is here referred to as a generic example of the structure of this type of article.

The article 10 comprises a central body or "chassis" 12 intended to be arranged according to a general basin configuration around the user's groin area. The central body 12 includes an absorbent core, sandwiched between a topsheet, which can be partially or totally permeable to body liquids and an impermeable lower sheet, or backsheet.

To allow the article 10 to be worn as pants, closed around the user's waistline, rear 16 and front 18 side panels are provided, respectively, connectable in the closed condition around the user's waistline by means of closing elements 20 placed, for example, at the distal margins of the rear side panels 16.

The side panels 16, 18 can be shaped or rectangular, for example, in the product structure shown in FIG. 1, both the rear side panels 16 and the front side panels 18 are shaped, typically in the form of a rectangular trapezoid, but in a common alternative embodiment, the front side panels 18 may, for example, be rectangular.

The side panels 16, 18, therefore, form part of the front and rear waist regions of the absorbent sanitary article 10, and are often provided with elastic elements in order to give the article better adherence to the user's body. These elastic elements are typically incorporated into the side panels according to known techniques, in general when forming the side panels themselves.

Generally, the side panels 16, 18, both of the elasticized and the non-elasticized type, are made from continuous webs of composite or stratified materials, and are then applied to the chassis 12, generally to a continuous web of composite material from which the individual chassis are subsequently obtained, or more commonly, to a continuous web of material intended to be part of the chassis 12 in a subsequent formation step, such as, for example, a continuous web of material intended to form the topsheet.

Elasticized side panels are obviously more expensive than those that do not have this characteristic, both due to the greater complexity of construction, and for the need to incorporate more valuable and expensive materials into the structure, typically elastic materials in the form of films or filaments, combined with non-elastic materials, typically consisting of nonwoven fabrics and/or polymeric films. Therefore for average or economically-priced sanitary articles, excluding therefore those of the "premium" category, a satisfactory compromise between quality and price can be represented by a combination of elasticized rear panels and non-elasticized front panels.

However, traditional production systems generally provide two distinct types of device, incorporated into the production line, for separately producing the elasticized rear panels and the non-elasticized front panels, typically due to the diversity of the materials used and of the respective structures.

The use of a single device would, of course, be advantageous in terms of reduced complexity and cost of the production line, but it is generally not feasible as it would involve producing both rear and front elasticized side panels, which may not be compatible with producing sanitary articles of average or economic price, or—alternatively—producing articles with non-elasticized panels, which however advantageous from the point of view of cost may not ensure the required quality of the final product in terms of comfort and effectiveness.

OBJECT AND SUMMARY OF THE INVENTION

The present invention aims to provide an apparatus and a method for producing side panels for applying to absorbent sanitary articles wearable as pants, which allows elasticized and non-elasticized side panels to be produced, by means of a single device incorporated in the production line.

According to the present invention, this object is achieved, by a method and by an apparatus having the characteristics forming the subject of the attached claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

DETAILED DESCRIPTION

Embodiments described herein, with reference to the figures, refer to a method and an apparatus for producing elasticized composite panels 16 and non-elasticized panels 18 for an absorbent sanitary article 10. According to possible embodiments, the elasticized composite panels 16 and the non-elasticized panels 18 may form the side panels of an absorbent sanitary article 10.

According to a possible embodiment, the method comprises: feeding a sheet 46 having side edges along a feed direction; forming controlled activation zones 152 in the sheet 46 within the side edges, spaced apart from each other along the feed direction, wherein each of the controlled activation zones 152 comprises activation elements selected in an assembly consisting of cuts 154, 156, holes 158, mechanical deformation 160, and combinations thereof; attaching elastic elements 68 onto the sheet 46 at respective controlled activation zones 152 to form a composite web 46'; making transverse cuts 182, 182', 82, 82*a*, 82*b*, 82' at predetermined intervals on the composite web 46' each crossing at least part of one of the controlled activation zones 152 to form elasticized composite panels 16 comprising at least part of an elastic element 68, and non-elasticized panels 18.

The activation elements make the sheet 46 extensible in a direction perpendicular to the feed direction at the controlled activation zones 152. They also have the advantage of creating a simpler fastening of the elastic element 68 to the sheet 46, and of effectively using the combined action of the elastic element 68 with the controlled activation zone 152 of the sheet 46 in the elasticized composite panels 16.

According to possible embodiments, the transverse cuts 182, 182' may form elasticized composite panels 16 and non-elasticized panels 18 from the composite strip 46' without producing scraps, thus with a lower use of materials.

According to possible embodiments, the transverse cuts 82, 82*a*, 82*b*, 82' can remove transverse portions 84, 84' from the composite web 46', which comprise at least one part of the controlled activation zones 152, to form the composite elasticized panels 16 and the non-elasticized panels 18. These portions 84, 84' can be rejected as scrap.

According to possible embodiments, the removed transverse portions 84, 84' can comprise at least one part of the respective elastic elements 68.

Figure 6A:
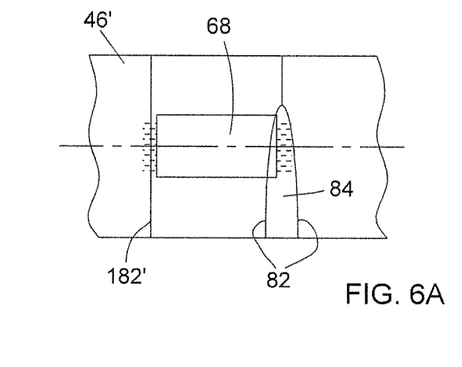
FIGS. 6A and 6B show a detail of two further possible embodiments of the method of the present invention.
Figure 6B:
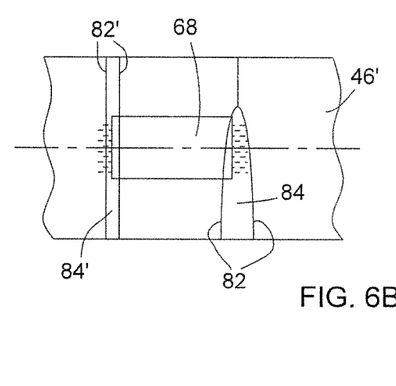
Figure 8:
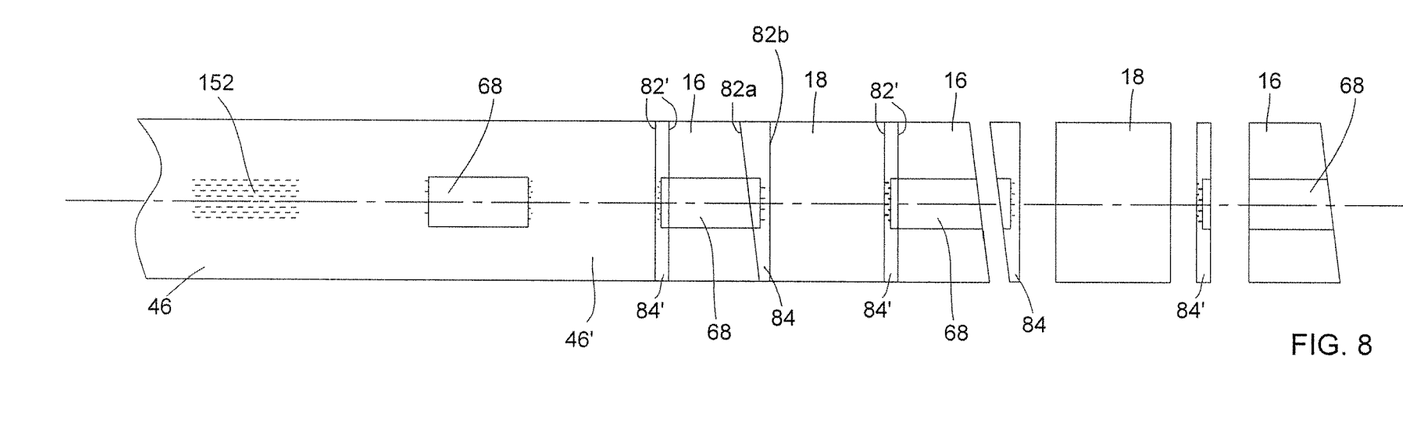
FIG. 8 shows a schematic plan view of the steps of the method according to another embodiment of the invention.

The removal of transverse portions 84, 84' from the composite web 46', comprising at least one part of the controlled activation zones 152 and of the respective elastic elements 68 has the advantage of forming elasticized composite panels 16 and non-elasticized panels 18 having more regular transverse edges, made from cuts 82, 82*a*, 82*b*, 82' as shown, for example, in FIGS. 6B and 8, even though due to the scraps it may involve a slightly greater use of material.

According to possible embodiments, the activation elements of the controlled activation zones 152 may comprise cuts 154, 156, which are advantageous as they do not entail removal of material from the sheet 46.

According to possible embodiments, the activation elements may comprise discontinuous cuts 154.

According to possible embodiments, the discontinuous cuts 154 can be aligned in rows parallel to each other.

According to possible embodiments, the discontinuous cuts 154 can be aligned in rows parallel and offset to each other.

According to possible embodiments, the activation elements may comprise continuous cuts 156.

According to possible embodiments, the continuous cuts 156 can be aligned in rows parallel to each other.

According to possible embodiments, the activation elements of the controlled activation zones 152 may comprise holes 158, which are advantageous in that they give the sheet 46 extensibility at the controlled activation zones 152, with a better resistance to stresses.

According to possible embodiments, the holes 158 can be circular.

According to possible embodiments, the holes 158 may have an elongated shape with a major dimension orientated in the feed direction, so as to give the sheet 46 a greater extensibility in a direction perpendicular to their major dimension.

According to possible embodiments, the holes 158 can be arranged in parallel rows with each other.

According to possible embodiments, the holes 158 can be arranged in parallel rows offset from each other.

According to possible embodiments, the activation elements of the controlled activation zones 152 may comprise a mechanical deformation 160 of the sheet 46, which is advantageous in that it gives the sheet 46 extensibility at the controlled activation zones 152, maintaining the continuity of the sheet 46 itself, without the need to create holes or cuts.

According to possible embodiments, the mechanical deformation 160 can be obtained by stretching the sheet 46 at least in a direction perpendicular to the feed direction, at the controlled activation zones 152 until a permanent elongation is achieved at these zones.

According to possible embodiments, the controlled activation zones 152 can be formed in the sheet 46 spaced from each another along the feed direction by a pitch P that can be fixed or variable, or alternated, or with sections with a first pitch alternated with sections with a second pitch different from the first, and combinations thereof.

According to possible embodiments, the elastic elements 68—in a relaxed condition—may extend at least partly beyond the controlled activation zones 152 in a direction perpendicular to the feed direction of the sheet 46 and towards both the side edges.

According to possible embodiments, the elastic elements 68 can be attached to the sheet 46 at least at the zones where they extend beyond the controlled activation zones 152 in a direction perpendicular to the feed direction of the sheet 46 and towards the side edges.

According to possible embodiments, the controlled activation zones 152 may have a maximum transverse dimension between 15% and 90% of the width of the sheet 46.

According to possible embodiments, the controlled activation zones 152 may have a maximum transverse dimension between 20% and 50% of the width of the sheet 46, with the advantage of producing elasticized composite panels 16 with good characteristics of elasticity and robustness, with the possibility of using, in combination, a smaller amount of material for the elastic elements 68.

According to a possible embodiment, the method comprises: feeding a sheet 46 having side edges along a feed direction; forming openings 52 in the sheet 46 within the side edges spaced apart from each other along the feed direction; attaching elastic elements 68 onto the sheet 46 at respective openings 52 to form a composite web 46'; making transverse cuts 182, 182', 82, 82*a*, 82*b*, 82' at predetermined intervals on the composite web 46' each crossing at least part of one of the openings 52 to form elasticized composite panels 16 comprising at least part of an elastic element 68, and non-elasticized panels 18.

The openings 52 make the sheet 46 extensible at the openings themselves in a direction perpendicular to the feed direction. They also have the advantage of allowing the production of a simpler structure for the elasticized composite panels 16 comprising at least part of the elastic element 68.

According to possible embodiments, the transverse cuts 182, 182' may form elasticized composite panels 16 and non-elasticized panels 18 from the composite strip 46' without producing scraps, thus with a lower use of materials.

According to possible embodiments, the transverse cuts 82, 82a, 82b, 82' can remove transverse portions 84, 84' from the composite web 46', which comprise at least one part of the openings 52, to form the composite elasticized panels 16 and non-elasticized panels 18. These portions 84, 84' can be rejected as scrap.

According to possible embodiments, the removed transverse portions 84, 84' can comprise at least one part of the respective elastic elements 68.

According to possible embodiments, the transverse cuts 182, 182', 82, 82a, 82b, 82' can be straight.

Figure 7:
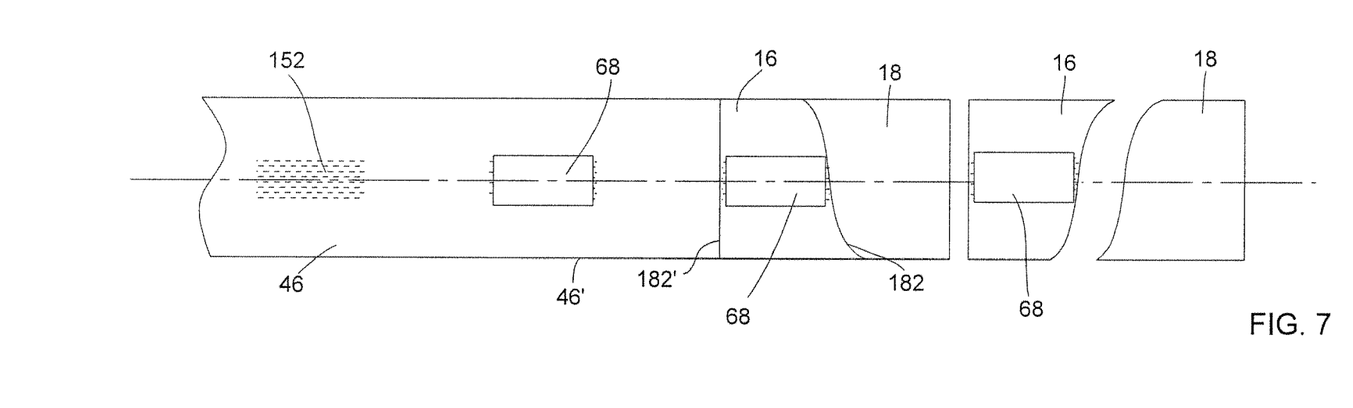
FIG. 7 is a schematic plan view of the steps of the method according to another embodiment of the invention.

According to possible embodiments, the transverse cuts 182, 182', 82, 82a, 82b, 82' can be curved, or may comprise straight and curved portions, so as to obtain shaped panels 16, 18, as illustrated by way of example in FIGS. 6A, 6B, 7.

Figure 2A:
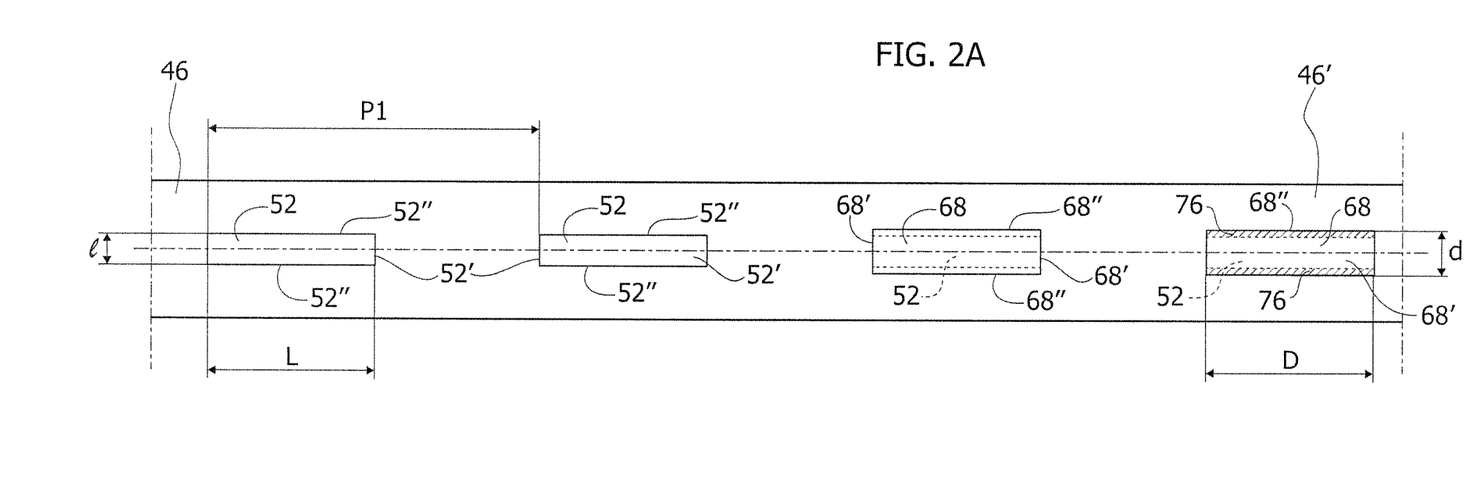
FIGS. 2A and 2B show a schematic plan view illustrating—in succession—the steps of the method according to an embodiment of the invention.
Figure 2B:
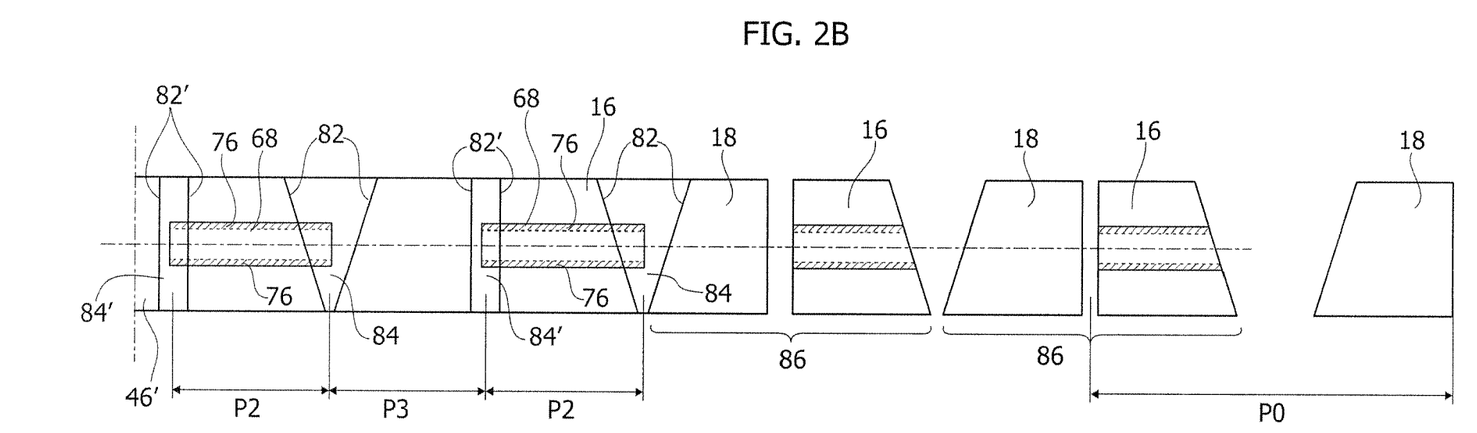
Figure 2C:
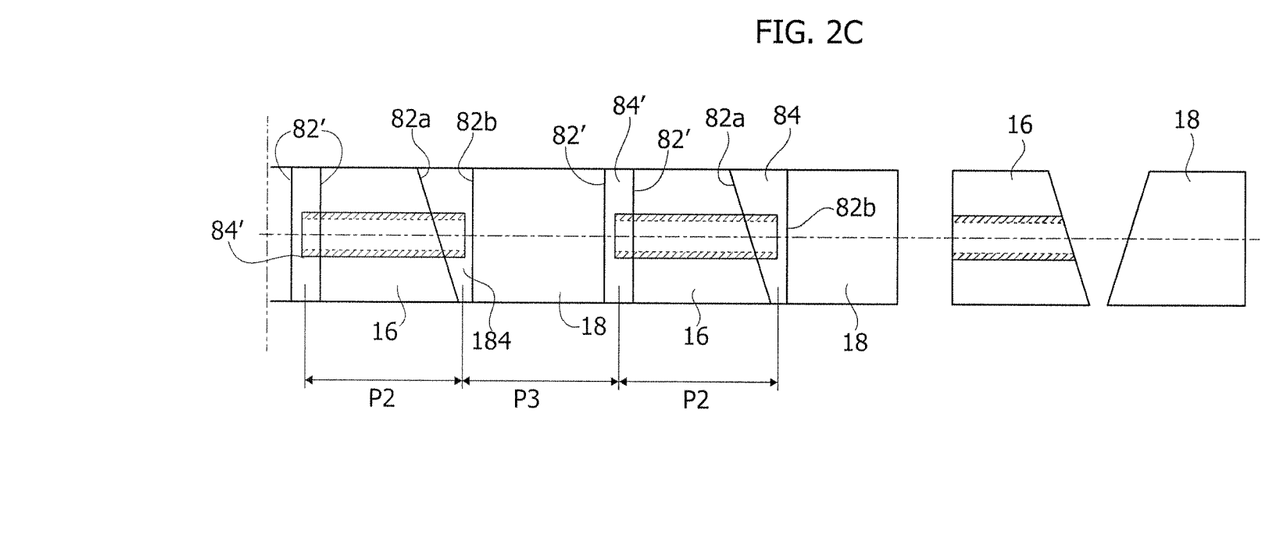
FIG. 2C is a schematic plan view corresponding to that of FIG. 2B, illustrating an alternative embodiment of the method of the present invention.

The removal of transverse portions 84, 84' from the composite web 46', comprising at least one part of the openings 52 and of the respective elastic elements 68 has the advantage of forming elasticized composite panels 16 and non-elasticized panels 18 having more regular transverse edges, made from cuts 82, 82a, 82b, 82' as shown, for example, in FIGS. 2B and 2C, even though, due to the scraps, it may involve a slightly greater use of material.

According to possible embodiments, the openings 52 can be formed in the sheet 46 spaced from each another along the feed direction by a pitch P that can be fixed or variable, or alternated, or with sections with a first pitch alternated with sections with a second pitch different from the first, and combinations thereof.

According to possible embodiments, the elastic elements 68—in a relaxed condition—may extend at least partly beyond the openings 52 in a direction perpendicular to the feed direction of the sheet 46 and towards both the side edges.

According to possible embodiments, the elastic elements 68 can be attached to the sheet 46 at least at the zones where they extend beyond the openings 52 in a direction perpendicular to the feed direction of the sheet 46 and towards the side edges.

Figure 4:
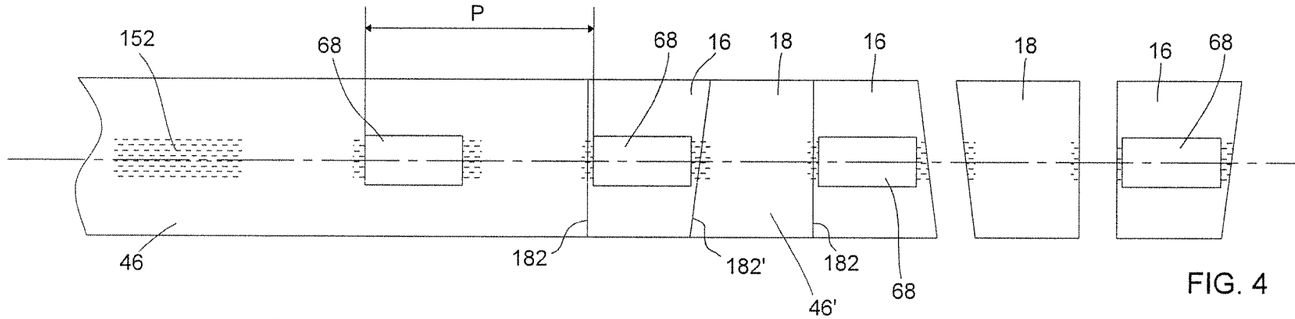
FIG. 4 is a schematic plan view of the steps of the method according to another embodiment of the invention.
Figure 5A:
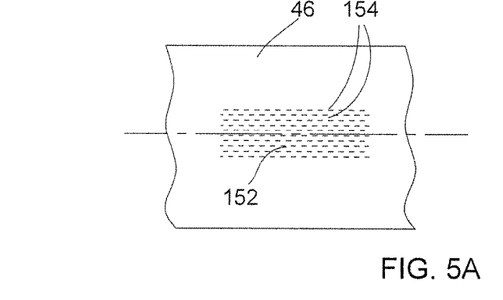
FIGS. 5A, 5B, 5C and 5D illustrate some possible embodiments of a step of the method of the present invention.
Figure 5B:
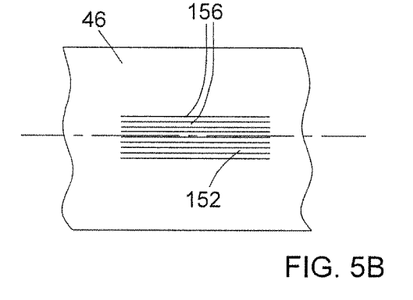
Figure 5C:
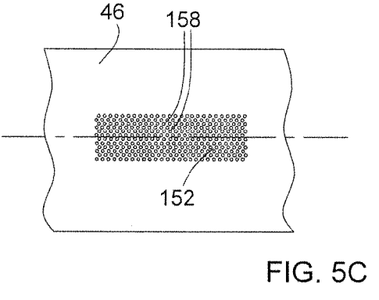
Figure 5D:
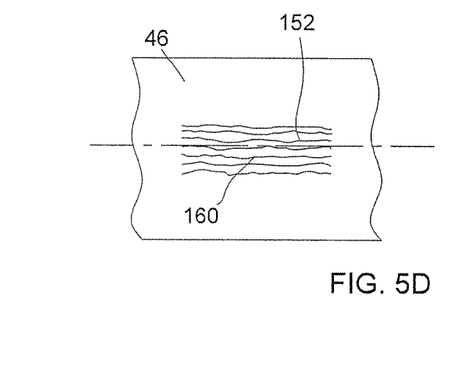

According to possible embodiments, each of the elastic elements 68 can be entirely included between two consecutive transverse cuts 182, 182', as shown by way of example in FIG. 4.

According to possible embodiments, the elastic elements can be elastically extensible at least in the direction perpendicular to the feed direction of the web 46.

According to possible embodiments, the openings 52 may have a maximum transverse dimension between 15% and 90% of the width of the sheet 46.

According to possible embodiments, the openings 52 may have a maximum transverse dimension between 20% and 50% of the width of the sheet 46, with the advantage of producing elasticized composite panels 16 with good characteristics of elasticity and robustness, with the possibility of using, in combination, a smaller amount of material for the elastic elements 68, and reducing the scraps due to the formation of the openings 52 in the sheet 46.

In accordance with possible embodiments, the present invention also relates to an apparatus 30 for producing elasticized composite panels 16 and non-elasticized panels 18 for an absorbent article, comprising: a first feed unit 32 for feeding a sheet 46 having side edges along a feed direction; a controlled activation unit 134 for forming controlled activation zones 152 in the sheet 46 within the side edges spaced apart from each other along the feed direction, comprising means for creating activation elements in the sheet 46 selected in an assembly consisting of: cuts 154, 156, holes 158, mechanical deformation 160, and combinations thereof; a unit 40 for attaching elastic elements 68 onto the sheet 46 at respective controlled activation zones 152 to form a composite web 46'; a second cutting unit 42 for making transverse cuts 182, 182', 82, 82a, 82b, 82' at predetermined intervals on the composite web 46' each crossing at least part of one of the controlled activation zones 152 to form elasticized composite panels 16 comprising at least part of the elastic element 68, and non-elasticized side panels 18.

The activation elements make the sheet 46 extensible in a direction perpendicular to the feed direction at the controlled activation zones 152. They also have the advantage of creating a simpler fastening of the elastic element 68 to the sheet 46, and of effectively using the combined action of the elastic element 68 with the controlled activation zone 152 of the sheet 46 in the elasticized composite panels 16.

According to possible embodiments, the transverse cuts 182, 182' may form elasticized composite panels 16 and non-elasticized panels 18 from the composite strip 46' without producing scraps, thus with a lower use of materials.

According to possible embodiments, the transverse cuts 82, 82a, 82b, 82' can remove transverse portions 84, 84' from the composite web 46', which comprise at least one part of the controlled activation zones 152, to form the composite elasticized panels 16 and non-elasticized panels 18. These portions 84, 84' can be rejected as scrap.

According to possible embodiments, the removed transverse portions 84, 84' may comprise at least one part of the respective elastic elements 68.

The removal of transverse portions 84, 84' from the composite web 46', comprising at least one part of the controlled activation zones 152 and of the respective elastic elements 68 has the advantage of forming elasticized composite panels 16 and non-elasticized panels 18 having more regular transverse edges, made from cuts 82, 82a, 82b, 82' as shown, for example, in FIGS. 6B and 8, even though due to the scraps it may involve a slightly greater use of material.

According to possible embodiments, the second cutting unit 42 of the apparatus 30 may comprise a device 43 for removing the scraps created by the transverse cuts 82, 82a, 82b, 82', i.e. the transverse portions 84, 84' removed from the composite web 46'.

According to possible embodiments, the activation elements of the controlled activation zones 152 may comprise cuts 154, 156, which are advantageous as they do not entail removal of material from the sheet 46.

According to possible embodiments, the activation elements may comprise discontinuous cuts 154.

According to possible embodiments, the discontinuous cuts 154 can be aligned in rows parallel to one another.

According to possible embodiments, the discontinuous cuts 154 can be aligned in rows parallel and offset to each other.

According to possible embodiments, the activation elements may comprise continuous cuts 156.

According to possible embodiments, the continuous cuts 156 can be aligned in rows parallel to each other.

According to possible embodiments, the activation elements of the controlled activation zones 152 may comprise holes 158, which are advantageous in that they give the sheet 46 extensibility at the controlled activation zones 152, with a better resistance to stresses.

According to possible embodiments, the holes 158 can be circular.

According to possible embodiments, the holes 158 may have an elongated shape with a larger dimension orientated in the feed direction, so as to give the sheet 46 a greater extensibility in a direction perpendicular to their major dimension.

According to possible embodiments, the holes 158 can be arranged in parallel rows with each other.

According to possible embodiments, the holes 158 can be arranged in parallel rows offset from each other.

According to possible embodiments, the activation elements of the controlled activation zones 152 may comprise a mechanical deformation 160 of the sheet 46, which is advantageous in that it gives the sheet 46 extensibility at the controlled activation zones 152, maintaining the continuity of the sheet 46 itself, without the need to create holes or cuts.

According to possible embodiments, the mechanical deformation 160 can be obtained by stretching the sheet 46 in a direction perpendicular to the feed direction, at least at the controlled activation zones 152 until a permanent elongation is achieved in these zones.

According to possible embodiments, the controlled activation zones 152 can be formed in the sheet 46 spaced from each another along the feed direction by a pitch P that can be fixed or variable, or alternated, or with sections with a first pitch alternated with sections with a second pitch different from the first, and combinations thereof.

According to possible embodiments, the elastic elements 68—in a relaxed condition—may extend at least partly beyond the controlled activation zones 152 in a direction perpendicular to the feed direction of the sheet 46 and towards both the side edges.

According to possible embodiments, the elastic elements 68 can be attached to the sheet 46 at least at the zones where they extend beyond the controlled activation zones 152 in a direction perpendicular to the feed direction of the sheet 46 and towards the side edges.

According to possible embodiments, the controlled activation zones 152 may have a maximum transverse dimension between 15% and 90% of the width of the sheet 46.

According to possible embodiments, the controlled activation zones 152 may have a maximum transverse dimension between 20% and 50% of the width of the sheet 46, with the advantage of producing elasticized composite panels 16 with good characteristics of elasticity and robustness, with the possibility of using, in combination, a smaller amount of material for the elastic elements 68.

According to a possible embodiment, the apparatus 30 for producing elasticized composite panels 16 and non-elasticized panels 18 comprises: a first feeding unit 32 for feeding a sheet 46 having side edges along a feed direction; a first cutting unit 34 for forming openings 52 in the sheet 46, spaced apart from each other along the feed direction within the side edges; a unit 40 for attaching elastic elements 68 onto the sheet 46 at respective openings 52 to form a composite web 46'; a second cutting unit 42 for making transverse cuts 182, 182', 82, 82a, 82b, 82' at predetermined intervals on the composite web 46' each crossing at least part of one of the openings 52 to form elasticized composite panels 16 comprising at least part of an elastic element 68 and non-elasticized panels 18.

The openings 52 make the sheet 46 extensible at the openings themselves in a direction perpendicular to the feed direction. They also have the advantage of allowing the production of a simpler structure for the elasticized composite panels 16 comprising at least part of the elastic element 68.

According to possible embodiments, the first cutting unit 34 of the apparatus 30 may comprise a device 35 for removing the scraps created by cutting the openings 52.

According to possible embodiments, the transverse cuts 182, 182' may form elasticized composite panels 16 and non-elasticized panels 18 from the composite strip 46' without producing scraps, thus with a lower use of materials.

According to possible embodiments, the transverse cuts 82, 82a, 82b, 82' can remove transverse portions 84, 84' from the composite web 46', which comprise at least one part of the openings 52, to form the composite elasticized panels 16 and non-elasticized panels 18. These portions 84, 84' can be rejected as scrap.

According to possible embodiments, the removed transverse portions 84, 84' can comprise at least one part of the respective elastic elements 68.

According to possible embodiments, the transverse cuts 182, 182', 82, 82a, 82b, 82' can be straight.

According to possible embodiments, the transverse cuts 182, 182', 82, 82a, 82b, 82' can be curved, or may comprise straight and curved portions, so as to obtain shaped panels 16, 18, as illustrated by way of example in FIGS. 6A, 6B, 7.

The removal of transverse portions 84, 84' from the composite web 46', comprising at least one part of the openings 52 and of the respective elastic elements 68 has the advantage of forming elasticized composite panels 16 and non-elasticized panels 18 having more regular transverse edges, made from the cuts 82, 82a, 82b, 82' as shown, for example, in FIGS. 2B and 2C, even though, due to the scraps, it may involve a slightly greater use of material.

According to possible embodiments, the second cutting unit 42 of the apparatus 30 may comprise a device 43 for removing the scraps created by the transverse cuts 82, 82a, 82b, 82', i.e. the transverse portions 84, 84' removed from the composite web 46'.

According to possible embodiments, the openings 52 can be formed in the sheet 46 spaced from each another along the feed direction by a pitch P that can be fixed or variable, or alternated, or with sections with a first pitch alternated with sections with a second pitch different from the first, and combinations thereof.

According to possible embodiments, the elastic elements 68—in a relaxed condition—may extend at least partly beyond the openings 52 in a direction perpendicular to the feed direction of the sheet 46 and towards both the side edges.

According to possible embodiments, the elastic elements 68 can be attached to the sheet 46 at least at the zones where they extend beyond the openings 52 in a direction perpendicular to the feed direction of the sheet 46 and towards the side edges.

According to possible embodiments, each of the elastic elements 68 can be entirely included between two consecutive transverse cuts 182, 182', as shown by way of example in FIG. 4.

According to possible embodiments, the elastic elements can be elastically extensible at least in the direction perpendicular to the feed direction of the web 46.

According to possible embodiments, the openings 52 may have a maximum transverse dimension between 15% and 90% of the width of the sheet 46.

According to possible embodiments, the openings 52 may have a maximum transverse dimension between 20% and 50% of the width of the sheet 46, with the advantage of producing elasticized composite panels 16 with good characteristics of elasticity and robustness, with the possibility of using, in combination, a smaller amount of material for the elastic elements 68, and reducing the scraps due to the formation of the openings 52 in the sheet 46.

According to possible embodiments, the sheet 46 can be a continuous sheet.

According to possible embodiments, the composite web 46' can be a continuous composite web.

Figure 3:
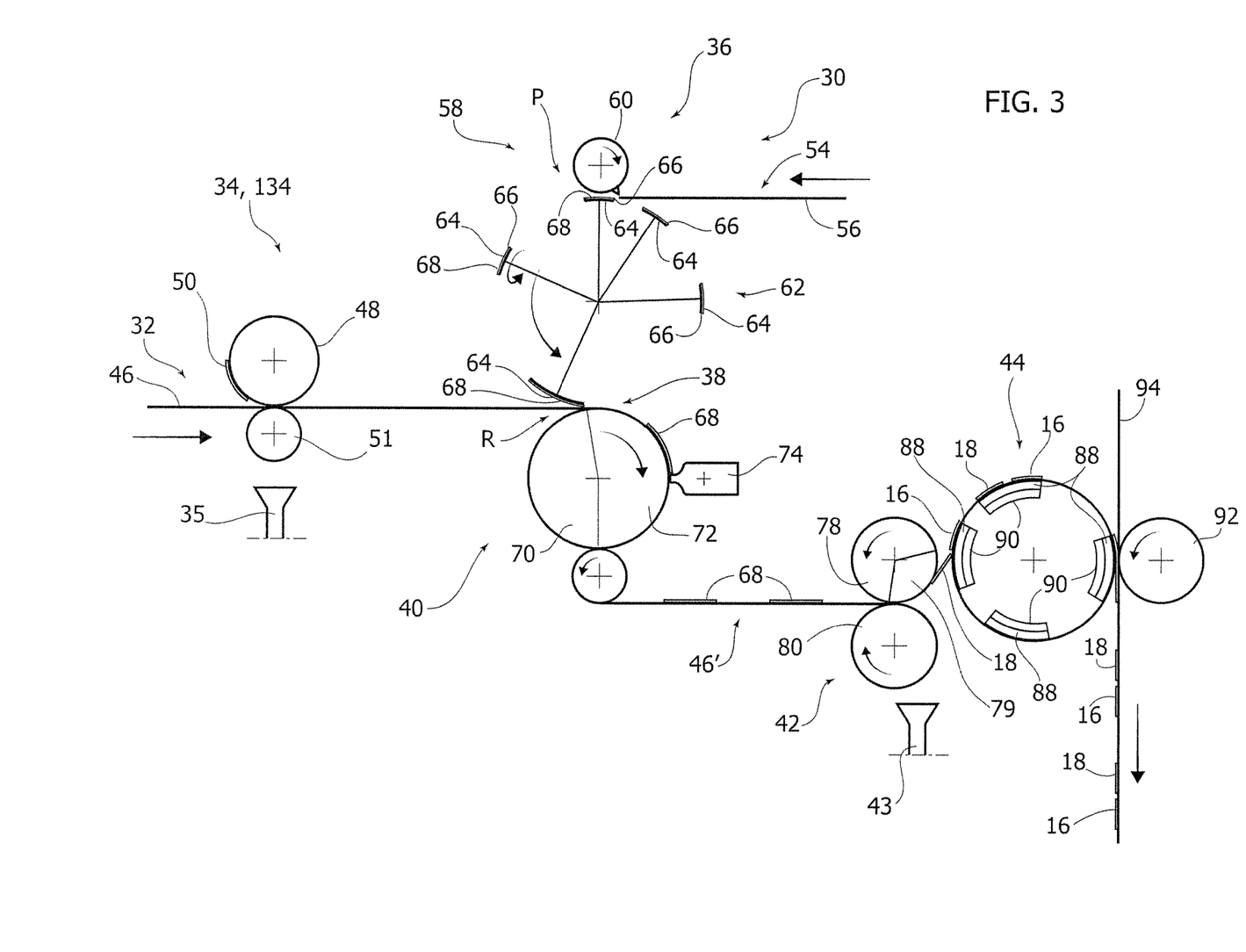
FIG. 3 is a schematic side view of an apparatus according to the present invention.

With reference to FIG. 3, numeral 30 indicates a possible embodiment of an apparatus for forming elasticized composite panels 16 and non-elasticized panels 18. The panels 16, 18 are intended to be incorporated as side panels in sanitary articles 10 wearable as pants, such as that illustrated by way of example in FIG. 1, and to form part of the front and rear waist regions of the sanitary articles 10. It should be noted that the apparatus 30 typically produces, starting from a first continuous sheet of non-extensible material 46, and as illustrated in greater detail in FIGS. 2A and 2B, rear 16 and front 18 side panels, intended to be applied to one of the longitudinal edges of the chassis 12. For example, with reference to the article of FIG. 1, the side panels 16 and 18 on the right or on the left. In a completely analogous manner, the rear and front side panels to be applied to the other longitudinal edge of the chassis 12 can generally be produced by an apparatus equivalent to the apparatus 30 operating in parallel and starting from a second continuous sheet of non-extensible material 46.

The apparatus 30 comprises a first feeding unit 32, a first cutting unit 34, a forming and feeding unit 36, a transfer unit 38, a welding unit 40, a second cutting unit 42 and a repitch and transfer unit 44.

The first feeding unit 32 feeds a first continuous sheet of non-extensible material 46, having longitudinal side edges, in the longitudinal direction. The first sheet 46 is non-extensible at least in a transverse direction, typically not extensible even in the longitudinal direction, and may preferably be of nonwoven fabric.

The first cutting unit 34 comprises a first knife roller 48 comprising, in turn, one or more cutting elements 50 cooperating with a first anvil roller 51 for making a plurality of oblong openings 52 in the first continuous sheet, at a pitch P1 and in a position within the respective longitudinal side edges, for example, rectangular openings, as illustrated in FIG. 2A, with the major axis substantially parallel to the longitudinal axis of the continuous web 46. By "substantially parallel" it is generally understood in the context of the present description that axes and/or segments that are "substantially parallel" to each other, for example, in this case the major axis of the oblong opening 52 and the longitudinal axis of the continuous sheet 46, can form an angle of not more than 30°, preferably not greater than 10°, and more preferably, they are parallel to each other. In the embodiments illustrated in FIGS. 2A, 2B and 2C, the typically rectangular openings 52 are transversely centered, i.e. they have the respective longitudinal axis substantially coincident with the longitudinal axis of the continuous sheet 46, but other configurations are possible, provided that the rectangular openings are positioned within the longitudinal edges of the continuous sheet 46. Each oblong opening 52 is generally elongated along the longitudinal axis of the continuous web 46, and may have, for example, a rectangular shape, or substantially rectangular with rounded corners, or can be oval or elliptical. Each oblong opening 52 has a maximum transverse dimension, i.e. in the direction perpendicular to the longitudinal axis of the continuous web 46, with a first length l, a maximum longitudinal dimension, or rather in the direction of the longitudinal axis of the continuous sheet 46, with a second length L and two longitudinal end zones. In the embodiment shown in FIGS. 2A, 2B and 2C, each oblong opening 52 has a rectangular shape and has two short sides 52' of the first length l, corresponding to the maximum transverse dimension, and two long sides 52" of the second length L, corresponding to the maximum longitudinal dimension, with the longitudinal end zones substantially corresponding to the two short sides 52'. Generally, the maximum transverse dimension of the oblong openings 52, in particular, for example, the first length l of the short sides 52' in the case of rectangular openings 52, can be between 15% and 90% of the total width of the continuous sheet 46, typically between 20% and 50%. The first cutting unit 34 typically also includes a device 35 for removing the scraps created by cutting the oblong openings 52, operating according to one of the methods known in the art, for example, by the action of suction and/or blowing compressed air.

The forming and feeding unit 36 comprises, in the embodiment illustrated in FIG. 3, a second feeding unit 54 for feeding a continuous elastic web 56 extensible in a longitudinal direction and having a width D. The forming and feeding unit 36 comprises a cutting, orientation, and pitch variation unit 58, typically referred to as a cutting, orientation and repitch unit, comprising a knife roller 60 and a rotating orientation and repitch device 62. The knife roller 60 comprises one or more cutting elements cooperating with anvils 66 of the rotating orientation and repitch device 62 for transversely cutting the continuous elastic web 56 while it is held in a substantially relaxed state, and forming therefrom a plurality of rectangular elements 68 of elastic material having a first dimension d in the longitudinal direction and a second dimension D in a transverse direction, equal to the width D of the continuous elastic web 56. Each rectangular element 68 has two minor sides 68' with said first dimension d greater than the first length l of the oblong openings 52 of the continuous sheet 46, in particular of the short sides 52' of the rectangular openings 52 in the illustrated embodiment, and two longer sides 68" with the second dimension D equal to the width of the continuous elastic web 56 and at least equal to the second length L of the oblong openings 52, in particular of the long sides 52" of the rectangular openings 52, as shown more clearly in FIG. 2A.

The continuous elastic web 56 may typically be an elastic film, or a laminated composite material, comprising e.g. filaments or webs of elastic material sandwiched between two continuous nonwoven sheets. According to a known technique, a composite elastic material of this type can be made by enclosing filaments or webs of elastic material in a tensioned state between two continuous nonwoven sheets and attaching the composite structure by means of welding and/or adhesive. The composite material thus produced, once brought back into a relaxed condition, is elastically extensible in the longitudinal direction, and can subsequently be fed—in said substantially relaxed state—to the cutting, orientation and repitch unit 58.

In an alternative embodiment of the present invention, the continuous elastic web 56 may consist of a continuous web of elastic material extensible in a transverse direction, i.e. in a direction substantially perpendicular to the respective longitudinal axis. In this case, the continuous elastic web 56 may typically have a width d, and the forming and feeding unit 36 may comprise the second feeding unit 54 and a cutting and pitch varying unit that cuts segments of elastic material with a length D from the continuous web, and of course of width d, determined by the width of the web, and it only varies the pitch, without the need to change the orientation by 90°.

Returning to the apparatus 30 of FIG. 3, the rotating orientation and repitch device 62 comprises a plurality of transport units 64 carried by a rotating support. In the illustrated embodiment, each transport unit 64 comprises an anvil 66 cooperating with the knife roller 60. The transport units 64 vary their rotational speed relative to the rotating support between a gripping position P and a release position R, remaining fixed in the radial direction, so as to perform the pitch variation. During rotation about the rotating support, the transport units 64 rotate by 90° about their own radial axis in the movement between the gripping position P and the release position R, as indicated in FIG. 3, so as to orientate the rectangular elements of elastic material 68 with the major sides 68" substantially parallel to the longitudinal axis of the continuous sheet 46, and, in the embodiment illustrated in FIG. 2A, to the long sides 52" of the rectangular openings 52 in the continuous sheet 46. The transport units 64 rotate again by 90° about their own radial axis in the subsequent movement between the release position R and the gripping position P. During rotation, the transport units 64 move cyclically between the gripping position P and the release position R. This type of repitch device is not imperative. Any other type of device may be used that is configured to separate successive discrete elements by a predetermined pitch, for example, a rotating device in which the transport units are rotatably fixed with respect to the rotating support, and are movable in a radial direction between a gripping position and a release position, of the type described, for example, in U.S. Pat. No. 4,617,082. More generally, a device may be used in which the transport units move along a closed but not circular path, as an alternative to devices of the illustrated type rotating about an axis.

With reference to FIG. 3, each transport unit 64 picks up a rectangular element of elastic material 68 in the gripping position P after cutting, and holds it there by known means on the respective outer surface, which generally has the shape of a cylindrical sector, for example, by suction through holes present on said cylindrical surface, which communicate with a sub-atmospheric pressure source, according to a known technique. Each transport unit 64, after having orientated and placed the respective rectangular element of elastic material 68 at the pitch P1, it positions it in the release zone R on the continuous sheet 46 at each oblong opening 52, in a position substantially centered with respect thereto; that is, in such a way as to completely cover it, with the major sides 68" of each rectangular element 68 entirely superimposed on the two longitudinal edges of each oblong opening 52. In particular, in the embodiment illustrated in FIG. 2A, in which the oblong openings 52 are typically rectangular, the substantially centered position of each rectangular element 68 with respect to the respective opening 52 envisages that the major sides 68" of each rectangular element 68 are parallel to the respective long sides 52" of the respective rectangular opening 52 and that the longitudinal axis of the rectangular element 68 substantially coincides with the longitudinal axis of the rectangular opening. In this way, the longitudinal edges adjacent to the major sides 68" of each element 68 are entirely superimposed on the respective longitudinal edges adjacent to the long sides 52" of the respective rectangular opening 52. The transverse edges of each element 68, in the embodiment illustrated in FIG. 2A, substantially coincide with the transverse edges of the respective rectangular opening 52, or alternatively, they can be superimposed on them similarly to the longitudinal edges, by virtue of the required relationship between the respective widths 1 and L of the rectangular openings 52, and the dimensions d and D of the rectangular elements 68.

The transfer of the rectangular elements 68 takes place from each transport unit 64 of the rotating orientation and repitch device 62 on the continuous sheet 46, while this slides on the anvil roller 70 of the welding unit 40, for example, according to a known technique, progressively deactivating the suction on each transport unit 64 as it passes through the release zone, i.e. through the respective tangency zone with the anvil roller 70, in turn provided with a suction section 72 that extends radially from said tangency zone.

The welding unit 40 further comprises a welding head 74 cooperating with the anvil roller 70, which welds each rectangular element of elastic material 68 to the continuous sheet 46 along at least the respective longitudinal edges superimposed on the longitudinal edges of each oblong opening 52, for example, rectangular, making welding lines 76 as illustrated in FIG. 2A, so as to form a continuous composite web 46'.

The welds 76 can be made by one of the methods known in the art, for example, by thermal, thermomechanical, or ultrasonic welding, by means of adhesives, or combinations thereof. In a preferred embodiment, illustrated in FIG. 3, the welding unit 40 comprises an ultrasonic welding system in which the anvil roller 70 has a series of protruding projections with head surfaces that form welding surfaces cooperating with the sonotrode of the welding head 74. The protruding projections may have a cross-section that is, for example, rectangular or rhomboidal and generally aligned in two parallel longitudinal arrays to form the welding lines 76. Ultrasonic welding, as well as thermal or thermomechanical welding, has the advantage of not requiring the use of adhesives.

The continuous composite web 46' is subsequently fed to a second cutting unit 42 and finally to a repitch and transfer unit 44.

The second cutting unit 42 comprises a second knife roller 78 and a second anvil roller 80, which perform a series of transverse cuts 82, 82' on the continuous composite web 46', at predetermined intervals, as shown in FIG. 2B, so as to remove transverse portions 84, 84' from said continuous composite web 46', which comprise at least the two longitudinal end zones of each oblong opening 52, corresponding in said embodiment to the short sides 52' of each rectangular opening 52, and the corresponding minor sides 68' of each respective element 68 of elastic material, thus forming alternately individual elasticized composite panels 16 comprising both the first non-extensible continuous sheet 46 and the continuous elastic web 56 of the rectangular element 68, and individual non-elasticized panels 18 not including the elastic material, but formed by the first non-extensible continuous sheet 46. The second cutting unit 42 can also include a device 43 for removing the scraps created by the transverse cuts 82, 82', that is, the transverse portions 84, 84' removed from the continuous composite web 46' operating according to one of the methods known in the art, for example, by the action of suction and/or blowing compressed air.

The transverse portions 84, 84' made by the transverse cuts 82, 82' may have a different shape according to the required shape for the resulting side panels 16, 18. For example, the transverse portions 84, 84' may have a trapezoidal or rectangular shape, or alternatively, both. More specifically, the trapezoidal shape can be an isosceles, scalene or rectangular trapezium. In all these cases, the transverse cuts 82, 82' are typically straight, but alternatively they can also be curved, so as to obtain shaped side panels 16, 18, as is known in the art.

Each second transverse portion 84, 184 removed from the continuous composite web 46' may have a trapezoidal shape; in other words, every other transverse portion has a trapezoidal shape, while the transverse portion 84' immediately following each trapezoidal shaped transverse portion 84, 184 may have a rectangular shape.

In the embodiment shown in FIG. 2B, for example, the transverse sections 84' have a rectangular shape, with the transverse cuts 82' perpendicular to the longitudinal axis of the continuous composite web 46', while the transverse sections 84 have the shape of an isosceles trapezium, with the transverse cuts 82 obliquely forming the same angle with the longitudinal axis of the continuous composite web 46'. In this way, the resulting side panels 16 and 18 both have the shape of a rectangular trapezoid, corresponding to a sanitary article 10 such as that illustrated in FIG. 1. In particular, in the sanitary article 10 of FIG. 1, the side panels 16 are elasticized composite panels comprising a central portion formed by the continuous elastic web 56, and two side portions formed by the first non-extensible continuous sheet 46, while the side panels 18 are non-elasticized panels formed substantially from the first non-extensible continuous sheet 46, both types of panels corresponding to those illustrated in FIG. 2B.

In an alternative embodiment, illustrated in FIG. 2C, the transverse sections 84' are still rectangular, as in the configuration of FIG. 2B, while the transverse sections 184 are in the form of a rectangular trapezoid, with inclined transverse cuts 82a and the transverse cuts 82b perpendicular to the longitudinal axis of the continuous composite web 46'. In this case, the elasticized side panels 16 are in the form of a rectangular trapezium, as in the embodiment of FIG. 2B, while the non-elasticized side panels 18 have a rectangular shape. It is also possible, in additional embodiments not illustrated, that all the transverse sections are rectangular, so as to form side panels 16 and 18 that are also rectangular, or that, in an embodiment similar to that illustrated in FIG. 2B, the transverse sections 84 have the shape of a scalene trapezium, with the transverse cuts 82 of each section 84 forming different angles with respect to the longitudinal axis of the continuous composite web 46'.

In addition to the shape, as previously described, the side panels 16 and 18 may have different dimensions. Side panels 16 and 18 made according to the method of the present invention, and as shown, for example, in the sanitary article 10 illustrated in FIG. 1, typically have the same width corresponding substantially to that of the continuous composite web 46 from which they are obtained, fed to the apparatus 30. The length of the panels, for example, measured along the respective longitudinal edges, generally corresponding to the proximal edges along which the side panels 16, 18 are typically connected to the chassis 12, can be typically selected according to the ratio between the pitch P1 of the openings, for example, rectangular 52 and their length L. In the embodiment illustrated in FIGS. 2A, 2B and 2C, for example, the pitch P1 corresponds to twice the length L, and the side panels 16 and 18 have a length substantially equal to each other along the respective proximal borders. Of course, in the embodiment of FIG. 2B, the side panels 16 and 18 both have a substantially equal shape and respective dimensions, while in the embodiment of FIG. 2C, the dimensions may be slightly different as, although they have respective proximal edges of the same length, the side panels 16 are trapezoidal and the side panels 18 are rectangular, and therefore have a larger surface area.

Alternatively, if the pitch P1 is less than twice the length L of the rectangular openings, in other words if the openings 52, for example rectangular, of the continuous sheet 46 are spaced apart from each other by a distance that is less than their length L, typically the non-elasticized panels 18 are then shorter than the elasticized panels 16 along the respective proximal edges.

Of course, that said above is reflected in the pitch at which the transverse sections 84, 84' are made on the continuous composite web 46', and which can be measured, for example, on the longitudinal axis of the continuous composite web 46' at the intersection of the midpoint of the length of each respective section 84, 84' along said axis, as illustrated in FIGS. 2A and 2B. The pitch between two successive transverse sections 84 and between two successive transverse sections 84' are equal to the pitch P1, where, for clarity the transverse sections 84 are those corresponding to the head section of each opening 52, for example, rectangular, while the transverse sections 84' correspond to the tail section, with respect to the sliding direction of the continuous composite web 46'. The pitch between a transverse section 84' and the subsequent transverse section 84 is equal to P2, while between the latter and the subsequent transverse section 84', it is equal to P3, with P2+P3=P1. In the embodiment illustrated in FIGS. 2B and 2C there is substantially P2=P3=L=P1/2.

Returning to the description of the apparatus 30, the elasticized side panels 16 and the non-elasticized side panels 18 are successively transferred from the second cutting unit 42, for example, from the second knife roller 78, as shown in FIG. 3, to the repitch and transfer unit 44. For example, as illustrated in FIG. 3, each pair 86 comprising a non-elasticized side panel 18 and the immediately successive elasticized side panel 16 is transferred from the knife roller 78 to a respective transport unit 88 of the repitch and transfer unit 44 using known techniques, for example, by suitably adjusting the suction in the knife roller 78, by means of the respective suction section 79, and in the transport units 88, each, in turn, comprising a suction unit 90, for example, in the tangency zone the suction in the knife roller 78 ceases and starts to act instead in the respective transport unit 88 of the transfer and repitch unit 44. The transfer and repitch unit 44 is of a known type, for example, as illustrated in FIG. 3, is of a type substantially equivalent to that of the unit 58, apart from, of course, the ability to also vary the orientation of the respective transport units, not necessary in the unit 44. The aforementioned discussion with respect to the unit 58 regarding pitch variation techniques also applies to the transfer and repitch unit 44.

In the transfer and repitch unit 44, each pair 86 of side panels 16, 18 is placed at the final pitch P0, generally corresponding to the length of the individual sanitary article 10, and applied, for example, by means of a welding unit 92, to a longitudinal edge of a continuous web of material 94, which, as known, can be a continuous web of composite material consisting of a chain of chassis blanks 12, or a continuous web of a material intended to become part of the chassis 12 in a subsequent forming step, for example, a continuous web of material 94 intended to form the topsheet. Each pair 86 of side panels 16, 18 is typically applied along the respective longitudinal major sides, i.e. the proximal edges, to a longitudinal edge of the continuous web 94. A similar apparatus typically involves forming and applying side panels 16 and 18 along the opposite longitudinal edge of the continuous web of material 94.

The closing elements 20, of any type known in the art, can be applied to the continuous sheet 46 or to the continuous composite web 46' with known methods, for example, preferably upstream of the cutting unit 42, at a pitch P1 and in such a way as to be applied in the required position along the distal edges typically of the elasticized side panels 16.

The product obtained downstream of the welding unit 92 is typically a continuous composite web 94 with pairs of elasticized side panels 16 and non-elasticized side panels 18 applied along the respective longitudinal edges at a pitch P0, characteristic of the sanitary article 10 which constitutes the final product of the method and apparatus of the present invention and which is typically obtained from the continuous composite web 94, once the structure of the chassis is completed according to the prior art, by transverse cuts forming the individual articles 10. A particularly important characteristic of the present invention is that a single apparatus 30 is capable of simultaneously producing both elasticized composite panels 16 and non-elasticized panels 18 intended to be incorporated into a sanitary article 10.

According to a possible embodiment, the method for producing elasticized composite panels 16 and non-elasticized panels 18 for an absorbent sanitary article may comprise:

feeding a first sheet of non-extensible material 46 having longitudinal side edges extending along a first direction parallel to a longitudinal axis of the sheet 46, forming in the sheet 46—in a position within the longitudinal edges and at a pitch P1—a plurality of oblong openings 52 having a major axis substantially parallel to the longitudinal axis of the web 46, each opening 52 having a maximum transverse dimension with a first length l, a maximum longitudinal dimension with a second length L, and two longitudinal end zones, forming a plurality of elements 68 of elastic material having—in a relaxed condition—two minor sides 68' with a first dimension d greater than the first length l and two major sides 68" with a second dimension D at least equal to the second length L of the oblong openings 52, the elements of elastic material 68 being elastically extensible at least along the first dimension d, transferring each of the elements 68 of elastic material in a relaxed condition onto the sheet 46 at each oblong opening 52 and in a position centered with respect to the oblong opening 52, welding each element 68 to the sheet 46 along at least the respective longitudinal edges superimposed on the longitudinal edges of each oblong opening 52, so as to form a composite web 46', making transverse cuts 82, 82a, 82b, 82' at predetermined intervals on the composite web 46' so as to remove transverse portions 84, 84', 184 from the composite web 46' comprising the longitudinal end zones of each oblong opening 52 and the corresponding minor sides 68' of each respective element 68 of elastic material, and alternately forming individual elasticized composite panels 16 comprising elastic material, and individual non-elasticized panels 18.

According to possible embodiments, the elements 68 of elastic material can be rectangular elements. According to possible embodiments, each second transverse portion 84, 184 removed from the composite web 46' may have a trapezoidal shape with at least one side that is oblique with respect to the longitudinal axis of the composite web 46'.

According to possible embodiments, the transverse portion 84' following each of the trapezoidal cross-sectional portions 84, 184 may have a rectangular shape with two sides perpendicular to the longitudinal axis of the composite web 46'.

According to possible embodiments, each removed transverse portion 84, 84', 184 may have a rectangular shape with two sides perpendicular to the longitudinal axis of the composite web 46'.

According to possible embodiments, each of the oblong openings 52 may have a major axis coinciding with the longitudinal axis of the composite web 46'.

According to possible embodiments, the maximum transverse dimension of each of the oblong openings 52 may have the first length l between 15% and 90% of the width of the sheet 46.

According to possible embodiments, the maximum transverse dimension of each of the oblong openings 52 may have the first length l between 20% and 50% of the width of the sheet 46, with the advantage of producing elasticized composite panels 16 with good characteristics of elasticity and robustness, with the possibility of using, in combination, a smaller amount of material for the elastic elements 68, and reducing the scraps due to the formation of the openings 52 in the sheet 46.

According to possible embodiments, the oblong openings 52 can be rectangular, with two short sides 52' corresponding to the maximum transverse dimension and two long sides 52" corresponding to the maximum longitudinal dimension, and with the longitudinal end zones corresponding to the short sides 52'.

According to a possible embodiment, an apparatus 30 for producing elasticized composite panels 16 and non-elasticized panels 18 for an absorbent sanitary article may comprise:

a first feeding unit 32 for feeding a first non-extensible sheet 46 having longitudinal edges extending along a first direction parallel to the longitudinal axis of the web 46, a first cutting unit 34 comprising a first cutting element 48 and a first anvil element 51 for forming in the sheet 46—at a pitch P1 and in a position within the respective longitudinal edges—a plurality of oblong openings 52 with the major axis substantially parallel to the longitudinal axis of the sheet 46, each opening 52 having a maximum transverse dimension with a first length l, a maximum longitudinal dimension with a second length L, and two longitudinal end zones, a forming and feeding unit 36 for forming a plurality of elements 68 of elastic material having—in a relaxed condition—two minor sides 68' with a first dimension d greater than said first length l and two major sides 68" with a second dimension D at least equal to the second length L of the oblong openings 52, the elements of elastic material 68 being elastically extensible at least along the first dimension d, and for feeding them at a pitch P1, a transfer unit 38 for transferring each of the elements 68 of elastic material in a relaxed condition onto the sheet 46 at each oblong opening 52 and in a position centered with respect to each oblong opening 52, a welding unit 40 comprising an anvil element 70 and a welding head 74 cooperating with the anvil element 70 to weld each element of elastic material 68 to the sheet 46 along at least the respective longitudinal edges superimposed on the longitudinal edges of each oblong opening 52, so as to form a composite web 46', a second cutting unit 42 comprising a second cutting element 78 and a second anvil element 80 for making transverse cuts 82, 82a, 82b, 82' at predetermined intervals on said composite web 46' so as to remove transverse portions 84, 184, 84' from the composite web 46', comprising at least the longitudinal end zones of each oblong opening 52 and the corresponding minor sides 68' of each element 68 of elastic material, so as to form alternately individual elasticized composite panels 16 comprising the elastic material and individual non-elasticized panels 18.

According to possible embodiments, the elements 68 of elastic material can be rectangular elements.

According to possible embodiments, the cutting element 48 and the anvil element 51 of the first cutting unit 34 may comprise a knife roller 48 and an anvil roller 51, respectively.

According to possible embodiments, the anvil element 70 of the welding unit 40 may comprise an anvil roller 70.

According to possible embodiments, the cutting element 78 and the anvil element 80 of the second cutting unit 42 may comprise a knife roller 78 and an anvil roller 80, respectively.

According to possible embodiments, the second cutting unit 42 may alternately remove—from the composite web 46'—a transverse portion of trapezoidal shape 84, 184 with at least one oblique side with respect to the longitudinal axis of the composite web 46', and a subsequent transverse portion.

According to possible embodiments, the second cutting unit 42 may subsequently remove after each of the trapezoidal cross-section portions 84, 184, a transverse portion 84' having a rectangular shape with two sides orthogonal to the longitudinal axis of the composite web 46'.

According to possible embodiments, the forming and feeding unit 36 may comprise a second feeding unit 54 for feeding an elastic web 56 of elastic material extensible in the longitudinal direction, and a cutting, orientation and repitch unit 58 comprising a cutting element 60 and an orientation and repitch device 62 comprising a plurality of transport units 64 cooperating with the cutting element 60 for transversely cutting the elastic web 56 and forming a succession of discrete sections 68 with a first length d, orienting them by rotating them by 90° with respect to the longitudinal direction, and spacing them apart from each other by the pitch P1.

According to possible embodiments, the cutting element 60 of the cutting, orientation and repitch unit 58 may comprise a knife roller 60.

According to possible embodiments, the oblong openings 52 formed by the first cutting unit 34 may be rectangular, with two short sides 52' corresponding to the maximum transverse dimension, and two long sides 52" corresponding to the maximum longitudinal dimension, and in which the longitudinal end zones correspond to the short sides 52'.

According to possible embodiments, the elasticized composite panels 16 and the non-elasticized panels 18 may constitute the side panels of an absorbent sanitary article 10.

According to possible embodiments, the sheet 46 can be a continuous sheet.

According to possible embodiments, the composite web 46' can be a continuous composite web.

According to possible embodiments, the elastic web 56 can be a continuous elastic web.

Of course, without prejudice to the principle of the invention, the details of construction and the embodiments may be widely varied with respect to those described and illustrated, without thereby departing from the scope of the invention as defined by the claims that follow.

The invention claimed is:

1. A method for producing elasticized composite panels and non-elasticized panels for an absorbent sanitary article comprising:
   feeding a sheet having side edges along a feed direction;
   forming controlled activation zones in said sheet within the side edges spaced apart along the feed direction, wherein each of the controlled activation zones comprises activation elements selected from the group consisting of: cuts, holes, mechanical deformation, and combinations thereof;
   attaching discrete elastic elements onto the sheet spaced apart along the feed direction to form a composite web, each elastic element overlapping a respective one of the controlled activation zones;
   making transverse cuts at predetermined intervals on the composite web, each transverse cut crossing at least part of one of the controlled activation zones to form separate and alternating elasticized composite panels and non-elasticized panels, wherein: each elasticized composite panel includes comprising at least part of one of the elastic elements, and each non-elasticized panel does not include any part of the elastic elements.

2. A method according to claim 1, wherein the elastic elements in a relaxed condition extend at least partly beyond the controlled activation zones in a direction perpendicular to the feed direction towards both side edges.

3. A method according to claim 1, wherein the transverse cuts remove transverse portions comprising at least one part of the controlled activation zones from the composite web.

4. A method according to claim 1, wherein each of the elasticized composite panels includes one of the elastic elements that is not cut by the transverse cuts.

5. A method according to claim 1, wherein said elastic elements are elastically extensible at least in a direction perpendicular to said feed direction.

6. A method for producing elasticized composite panels and non-elasticized panels for an absorbent sanitary article comprising:
   feeding a sheet having side edges along a feed direction;
   forming openings in the sheet within the side edges spaced apart along the feed direction;
   attaching discrete elastic elements on the sheet spaced appart along the feed direction to form a composite web, each elastic element overlapping a respective one of the openings; and
   making transverse cuts at predetermined intervals on the composite web,. each transverse cut crossing at least part of one of the openings to form separate and alternating elasticized composite panels and non-elasticized panels, wherein: each elasticized composite panel includes at least part of one of the elastic elements, and each non-elasticized panel does not include any part of the elastic elements.

7. A method according to claim 6, wherein the elastic elements in a relaxed condition extend at least partly beyond the openings in a direction perpendicular to the feed direction towards both side edges.

8. A method according to claim 6, wherein the transverse cuts also form transverse portions that include at least a part of the openings from said composite web, the transverse portions being separate from the elasticized composite panels and the non-elasticized panels.

* * * * *